United States Patent [19]
Love et al.

[11] Patent Number: 5,522,885
[45] Date of Patent: Jun. 4, 1996

[54] ASSEMBLY TOOLING FOR AN AUTOLOGOUS TISSUE HEART VALVE

[75] Inventors: Charles S. Love, Newbury Park; Philip J. Hudak, Burbank; Robert W. Suggitt, Newbury Park, all of Calif.

[73] Assignee: Autogenics, Newbury Park, Calif.

[21] Appl. No.: 238,463

[22] Filed: May 5, 1994

[51] Int. Cl.$^6$ .................................................. A61F 2/24
[52] U.S. Cl. .............................. 623/2; 623/66; 623/901; 137/515.7; 251/365
[58] Field of Search ................................ 623/2, 66, 901; 137/515.7; 251/365; 29/213.1

[56] References Cited

U.S. PATENT DOCUMENTS

| | | |
|---|---|---|
| 3,548,418 | 12/1970 | Angell et al. . |
| 3,574,865 | 4/1971 | Hamaker ..................................... 623/2 |
| 3,587,115 | 6/1971 | Shiley . |
| 4,084,268 | 4/1978 | Ionescu et al. . |
| 4,182,446 | 1/1980 | Penny . |
| 4,247,292 | 1/1981 | Angell . |
| 4,297,749 | 11/1981 | Davis . |
| 4,364,127 | 12/1982 | Pierce et al. . |
| 4,443,895 | 4/1984 | Lane . |
| 4,470,157 | 9/1984 | Love . |
| 4,501,030 | 2/1985 | Lane . |
| 4,679,556 | 7/1987 | Lubock . |
| 4,692,164 | 9/1987 | Dzemeshkevich et al. . |
| 4,725,274 | 2/1988 | Lane . |
| 4,881,562 | 11/1989 | Wright . |
| 5,037,434 | 8/1991 | Lane . |
| 5,041,130 | 8/1991 | Cosgrove et al. .................... 623/2 |
| 5,163,955 | 11/1992 | Love . |
| 5,236,450 | 8/1993 | Scott .................................. 623/2 |
| 5,326,370 | 7/1994 | Love et al. . |
| 5,326,371 | 7/1994 | Love et al. . |
| 5,425,741 | 6/1995 | Lemp et al. . |

FOREIGN PATENT DOCUMENTS

| | | |
|---|---|---|
| 0357003 | 7/1990 | European Pat. Off. . |
| WO9115167 | 10/1991 | WIPO . |

OTHER PUBLICATIONS

Love et al, "The Autogeneous Tissue Heart Valve: Current Status", J. of Cardiac Surgery, vol. 6, No. 4, (1991), pp. 499–507.

Love et al., "Rapid Intraoperative Fabrication of an Autogeneous Tissue Heart Valve: A New Technique".

Reis et al., "The Flexible Stent", Reprint from the Journal of Thoracic and Cardiovascular Surgery, vol. 62, No. 5, pp. 683–689, Nov. 1971.

Bartek et al., "Frame–mounted Tissue Heart Valves: Technique and Construction", Thorax, 1974, vol. 29, pp. 51–55.

Black et al., "A Technique for Minimsing Valve Leaflet Fatigue Failure in Pericardial Valves", Proceedings XI Annual Meeting ESAO, Alpbach–Innsbruck, Austria, Sep. 1984.

Ionescu et al., "Replacement of Heart Valves with Frame––mounted Tissue Grafts", Thorax, 1974, vol. 29, pp. 56–67.

Love, "Pericardial Tissue as a Cardiac Valve Substitute", Proceedings of a Symposium, Thumersbach, Austria, Sep. 1988.

Yates, "A Fascial Frustrum Valve for Aortic Valve Replacement", Thorax, 1971, vol. 26, pp. 184–189.

*Primary Examiner*—Paul B. Prebilic
*Attorney, Agent, or Firm*—Knobbe, Martens, Olson & Bear

[57] ABSTRACT

An assembly tool for a bioprosthetic heart valve is disclosed. The tool assembles a valve having an inner and a spreadable outer stent, and includes a spreading ring with an elevated lip to hold the spread outer stent, an expander having fingers which contact the outer stent base to spread it apart, and a plunger to spread the fingers of the outer stent. An assembly mandrel having indexing rails allows the insertion of the inner stent into the spread outer stent while maintaining the correct rotational positioning of both stents. A shedding cap protects the tissue wrapped on the inner stent from abrasion during insertion.

11 Claims, 7 Drawing Sheets

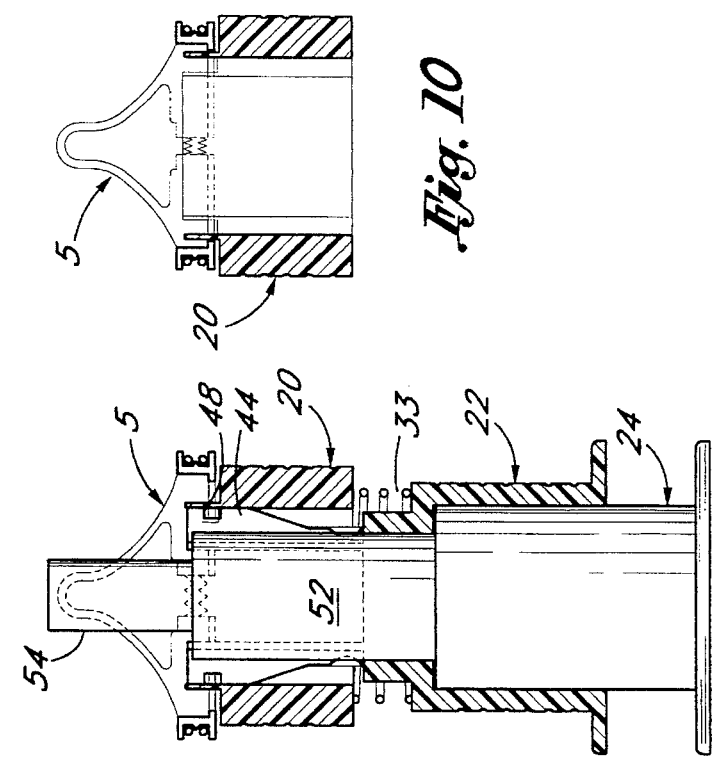
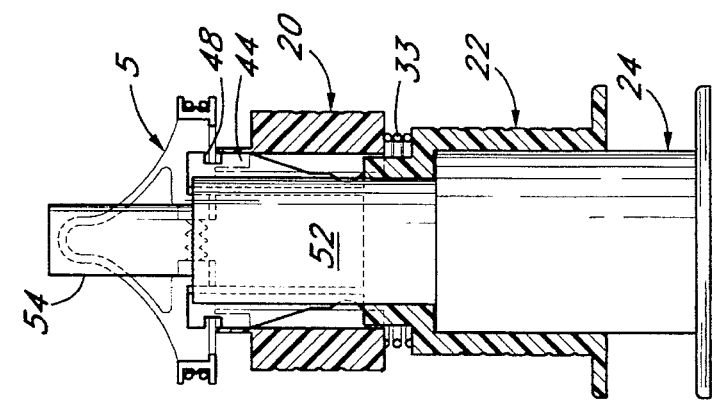
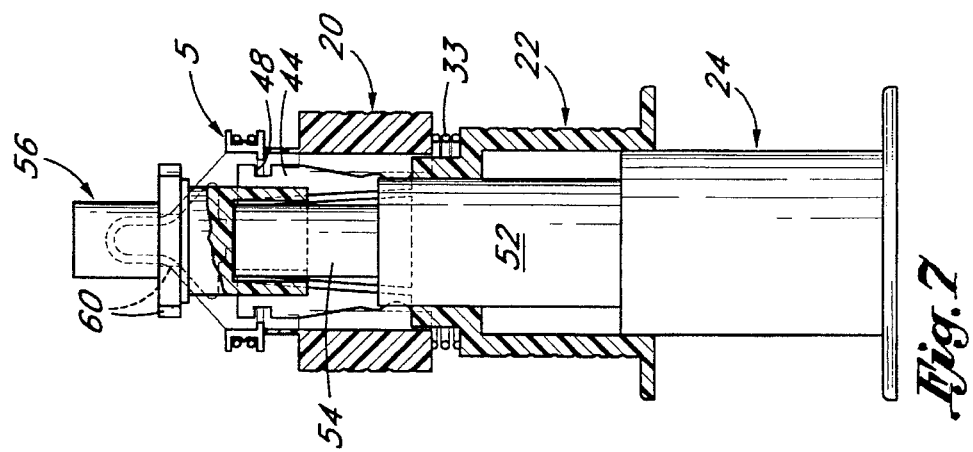

ASSEMBLY TOOLING FOR AN AUTOLOGOUS TISSUE HEART VALVE

BACKGROUND OF THE INVENTION

This invention relates to the fabrication of bioprosthetic heart valve replacements. Valve replacements are required for patients having a heart valve which is diseased or otherwise incompetent. Commonly, heart valve prostheses are made from a combination of either human or animal tissue and mechanical elements. These so-called "bioprostheses" have several advantages over purely mechanical valves or valves made only from tissue. Like mechanical valves, they are more durable than tissue valves but unlike mechanical valves they do not generally require that the patients undergo anticoagulant therapy for the rest of their lives.

U.S. Pat. No. 5,163,955 (the '955 patent), assigned to Autogenics, assignee of the present application, discloses such a bioprosthetic valve invention in which an inner stent, on which the autologous tissue used to construct the valve is wrapped, is inserted into a spreadable outer stent containing a self-adjusting tensioning spring around the circumference of its base. The spread outer stent clamps the stents together at its base and at a plurality of posts projecting from the bases of both the inner and outer stents. This clamping thus secures the tissue while compensating for irregularities in the tissue and supplying a clamping force which is evenly distributed over the entire circumference of the tissue.

The '955 patent, which is incorporated herein by reference, also discloses assembly tooling for mating the inner and outer stents. For the assembly method described in the '955 patent, a sleeve, a top spreading tool, and a spreading bullet are used to spread the outer stent and insert the tissue-wrapped inner stent into engagement with the inner surfaces of the outer stent. In use, the outer stent is pushed, bottom first, over the top of the spreading bullet. The bullet's ramped surfaces cause the outer stent to spread open until the bottom of the annular base of the outer stent rests on the ledge of the sleeve, which fits over the spreading bullet. The sleeve, which now holds the spread outer stent, is then removed from the spreading bullet. A mandrel holding the inner stent is inserted into the center of the sleeve, completing the assembly.

SUMMARY OF THE INVENTION

In accordance with the present invention, an improved tool is provided for assembling a bioprosthetic heart valve comprised of an inner stent covered with tissue and a spreadable outer stent with a plurality of posts and a spreadable base having three arcuate sections. The tool includes an annular spreading ring with inner and outer surfaces and an elevated lip configured to engage the annular base of the outer stent when it is in a spread position. The elevated lip is preferably provided with a lobed surface having a radius of curvature substantially equal to that of the unspread stent. These lobed surfaces advantageously support the arcuate sections of the outer stent base along their entire length when the outer stent is spread, thus evenly distributing the contact forces.

An annular expander, which has fingers attached to its top portion, mates with the inner surface of the annular spreading ring. The expander's fingers register with the ring's slots and contact the annular base of the outer stent. The fingers are movable from a rest position to a spread position, and spread the base of the outer stent when they are in the spread position. The fingers of the expander advantageously engage the outer stent base at the midpoint of each of the arcuate sections along the outer stent base, thereby optimally distributing the spreading force on each section of the outer stent base. A cylindrical plunger is inserted into the annular expander and forces its fingers into the spread position.

A protective cap is preferably fitted over the plunger. The cap has three slots for engaging the expander fingers and three cutouts for engaging the outer stent posts. This cap advantageously prevents rotation of the outer stent with respect to the expander fingers, thus keeping the fingers engaged with the center of each of the arcuate sections of the outer stent base.

After the outer stent has been spread, the elevated lip of the spreading ring is moved into contact with the inner surface of the base of the outer stent, thereby supporting it. This may be accomplished by the use of a spring mounted to the annular expander. The plunger is then removed from the spreading assembly. Next, the spreading ring, now supporting the spread outer stent, is removed from the expander assembly.

To complete the assembly process, the inner stent is placed atop a mandrel, having a base and a top portion configured to secure the inner stem in place. The mandrel is inserted into the inner surface of the spreading ring to mate the inner and outer stents. The bottom portion of the mandrel has a plurality of indexing rails which register with the slots on the spreading ring, providing positive rotational alignment of the inner and outer stents. As the mandrel is pushed through the spreading ring, the indexing rails also contact the base of the outer stent, disengaging it from the spreading ring's lip and completing the assembly. The indexing rails therefore advantageously ensure proper axial and rotational alignment of the inner and outer stent. A shedding cap, preferably mounted to the top portion of the mandrel, covers the tissue on the posts of the inner stent and prevents abrasion during the insertion process.

The assembly tooling and method of the present invention thus achieve the desired objectives of providing a repeatable method for assembling an autologous-tissue heart valve which can be performed quickly in an operating-room setting. The method of the present invention is easily performed by a surgeon or technician, does not require the use of large engagement forces, and provides positive indications of proper operation to the surgeon or technician.

BRIEF DESCRIPTION OF THE DRAWINGS

FIGS. 7–9 are cross-sectional views illustrating the spreading of the outer stent base.

FIG. 10 is a cross sectional view of the spreading ring holding the spread outer stent.

DETAILED DESCRIPTION OF THE PREFERRED EMBODIMENTS

Figure 1:
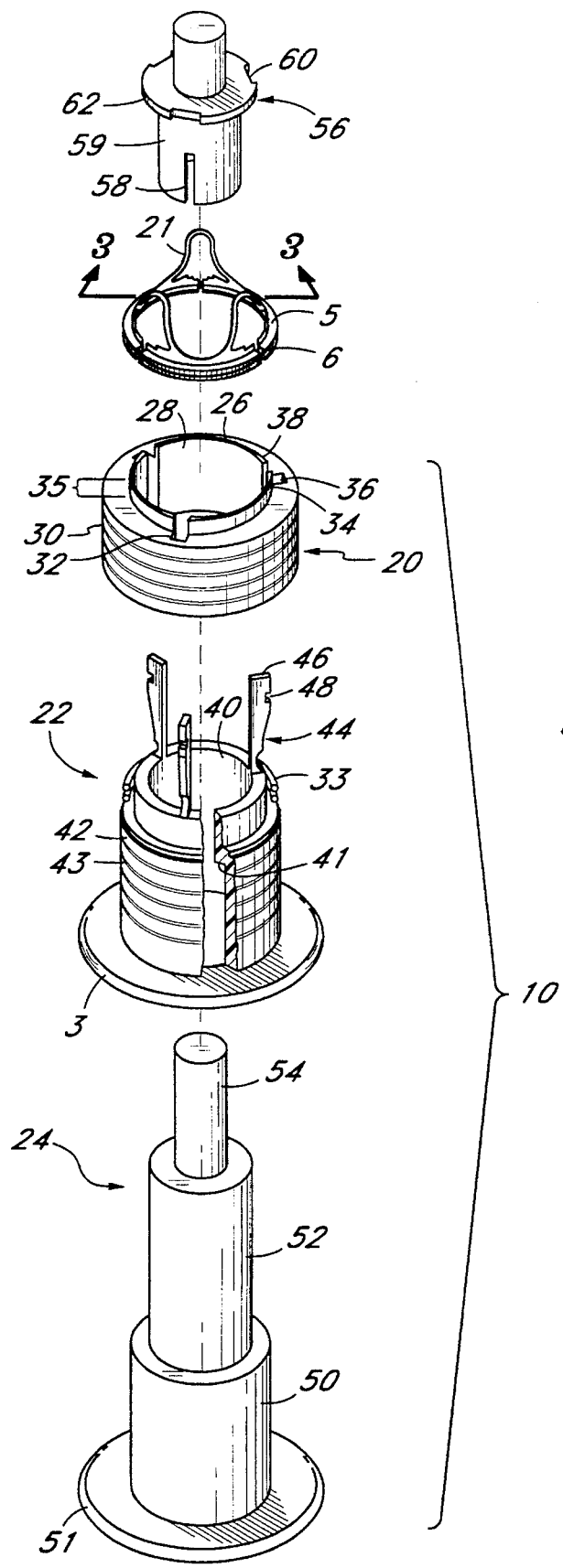
FIG. 1 is an exploded view of a portion of the assembly tool of the present invention.

Referring to FIG. 1, a spreading tool for moving an outer stent 5 to a spread position is depicted generally at 10. The spreading tool 10 is generally provided partially assembled in a size-specific kit, each part thereof having dimensions to match the size of the valve to be assembled. As described in the '955 patent, after the surgeon determines the correct heart valve size, he or she selects a correspondingly-sized kit, which includes an outer stent and an inner stent, each having the proper diameter.

Figure 2:
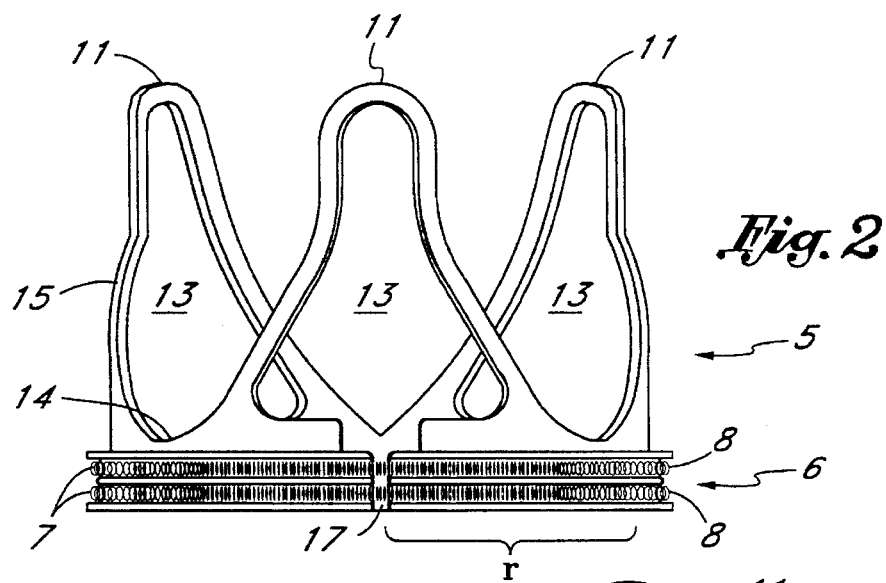
FIG. 2 is a side view of an outer stent shown in FIG. 1 for a bioprosthetic heart valve assembled by the tooling of the present invention.

The outer stent 5, which is the workpiece of the spreading tool 10, is depicted in more detail in FIG. 2. The outer stent 5 has an annular base 6 constructed with two grooves 7 around its outer periphery into which a self-adjusting tensioning means such as a garter spring 8 or the like is fitted. Two garter springs are preferably provided for redundancy. The assembly tool is advantageously used to operate on the inner and outer stents more fully set out in the present assignee's co-pending application Ser. No. 08/169,336, filed Dec. 17, 1993 and incorporated herein by reference.

The outer stent 5 has three posts 11 containing windows 13 which define a contour in the corresponding post of the outer stent frame and are surrounded by members such as 15, which give the post shape. The inner surface of the base 6 of the outer stent has a radius r, as shown in FIG. 2. The windows 13 facilitate the mating of the inner and outer stents by coinciding with the posts of the inner stent. Scalloped walls 14 separate the posts 13.

Figure 3:
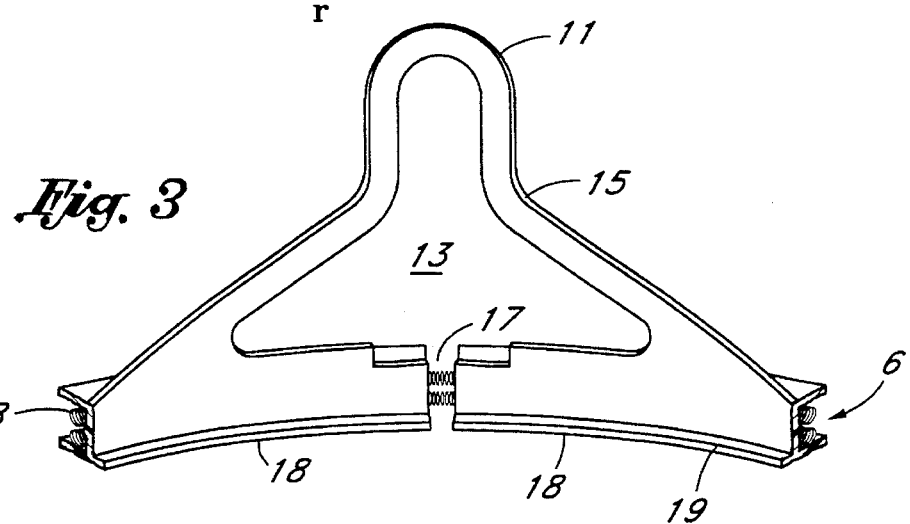
FIG. 3 is a view of the interior of the frame of the outer stent shown in FIG. 1.

Another aspect of the outer stent 5 is a window extension 17, which extends from the window 13 through the annular base of the outer stent. Preferably, one such extension is contained in every post of the outer stent. These window extensions 17 divide the outer stent 5 into three arcuate sections 18, and it is these extensions which allow the outer stent 5 to be spread by the assembly tool 10 of the present invention. In the preferred embodiment of the present invention, the outer stent base 6 includes an inner flange 19 on its inner surface, as shown in FIG. 3.

Figure 4:
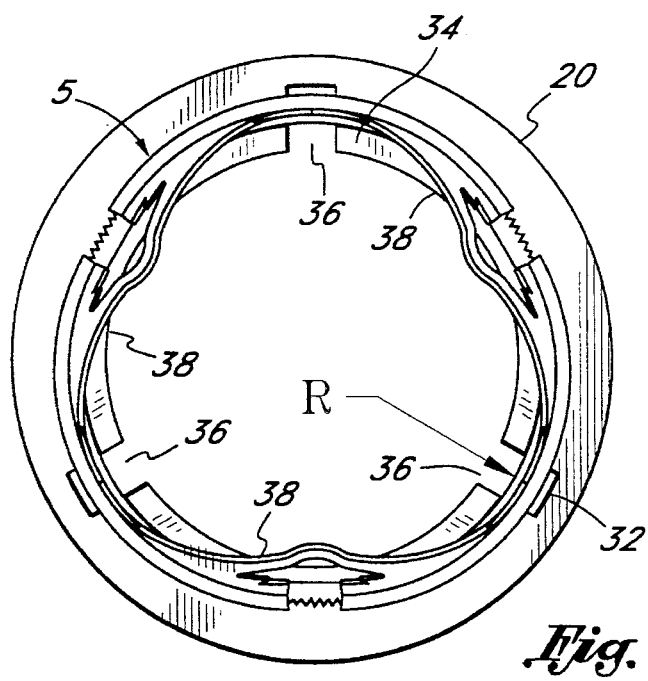
FIG. 4 is a plan view of the spreading ring illustrated in FIG. 2.
Figure 14:
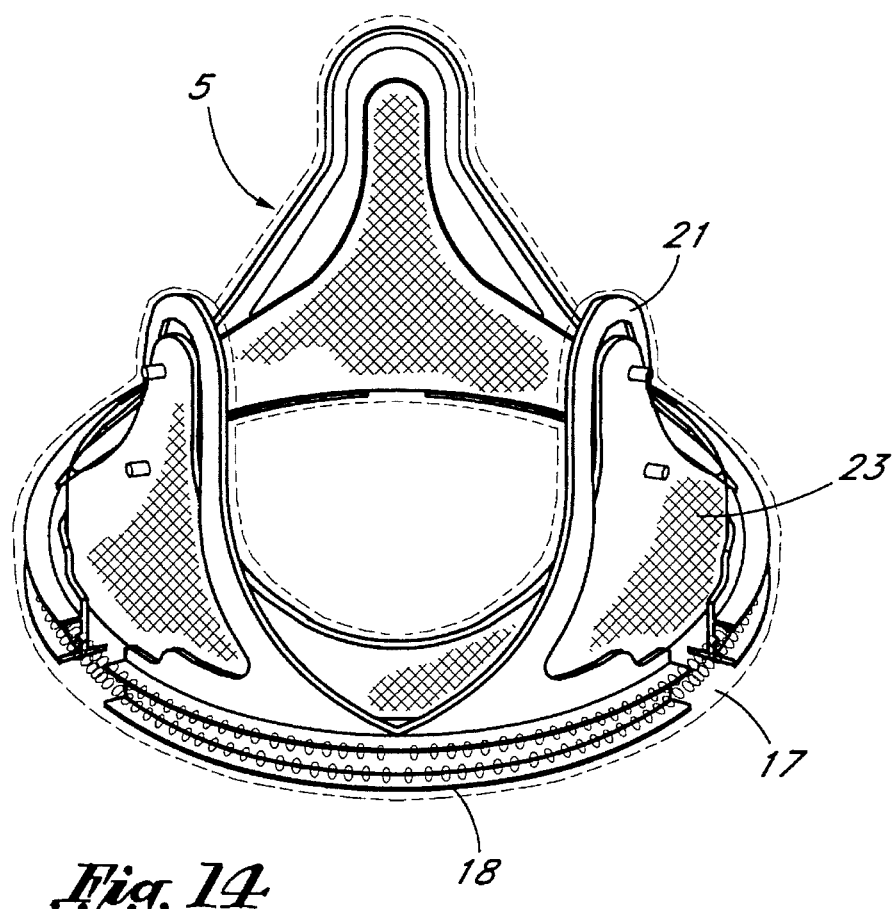
FIG. 14 is a view of the inner and outer stents of the present invention nested together.

As described below, the spreading tool 10 applies outward radial force to the base 6 of the outer stent. When this outward radial force is applied to the base 6, its arcuate sections 18 move radially outward from each other by increasing the width of the windows 17, forming a ring having an inner radius R, as shown in FIGS. 4 and 10, and composed of the individual arcuate sections 18 separated by the windows 17. The tensioning spring 8 resists this outward expansion, supplying tension to the posts of the outer stent 5 and cradling the inner stent 76 when the inner and outer stents are mated, as shown in FIG. 14. The outer stent 5 is covered with a sock 21, preferably made out of a material such as DACRON, which is then closed with thermally-bonded, overlapping fabric layers at the base of the stent, as discussed in the present assignee's co-pending application Ser. No. 08/169,336, filed Dec. 17, 1993.

Referring again to FIG. 1, the spreading tool 10 includes a spreading ring 20, an expander 22 and a plunger 24. Each of the components of the spreading assembly 10 is preferably constructed out of plastic, although many other materials are also suitable. The spreading ring 20 has an elevated lip 26 which engages and supports the inside portion of the base 6 of the outer stent when the expander 22 has applied an outward radial force to the outer stent 6. The body of the spreading ring 20 has a generally annular shape, with an inner surface 28 and an outer surface 30.

Coil spring 33 is advantageously located around the outer surface of the expander 22, beneath the spreading ring 20, to urge the elevated lip 26 into engagement with the outer stent base 6 when the outer stent has been spread. Axial slots 32 are cut into the inner surface 28 of the spreading ring, each preferably separated by 120 degrees. As will be seen later, these axial slots allow for the registry of the fingers of the expander 22 with the base 6 of the outer stent 5.

Figure 11:
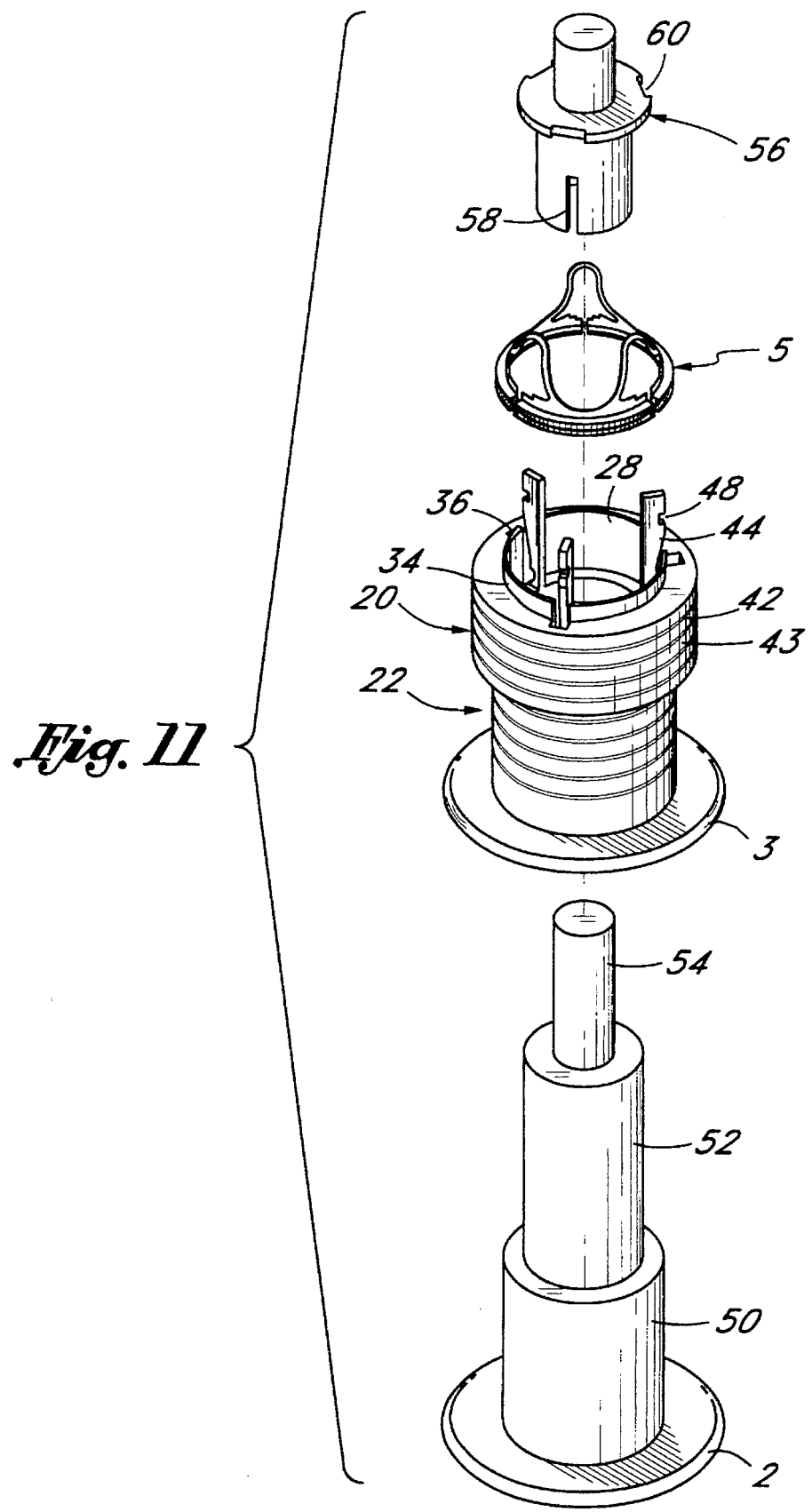
FIG. 11 is a perspective view of the assembly tool illustrated in FIG. 1.

A significant feature of the preferred embodiment of this invention is that the elevated lip 26 of the present invention has a plurality of lobed surfaces 34, as can be seen in FIG. 4. As described below, these lobed surfaces 34 uniformly distribute the stress placed upon the outer stent during the spreading operation. The lobed surfaces 34 have a circular circumferential profile having a radius of curvature equal to the radius r of the inner surface of the base of the unspread outer stent. Windows 36 in the lobed surfaces 34 are coincident with the axial slots 32 and allow the fingers of the expander to register with the inner surfaces of the outer stent 5, as shown in FIG. 11. In the preferred embodiment, these windows 36 bisect each of the lobed surfaces 34 and split the elevated lip 26 into a plurality of arcuate sections 38.

Figure 13:
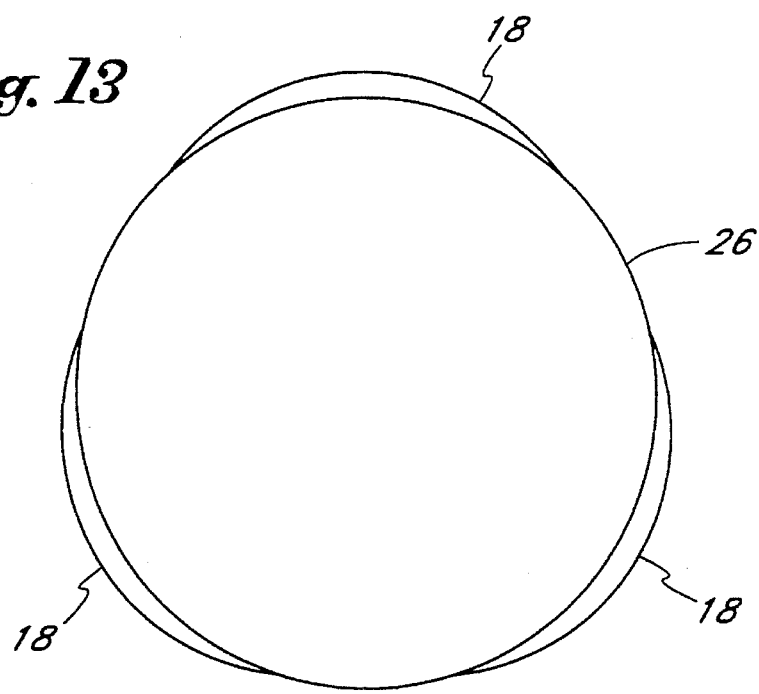
FIG. 13 is a view of the contact between the outer stent and a circular spreading ring lip.

When the elevated lip 26 is brought into contact with the inner surfaces of the base 6 of the spread outer stent, each of the lobed surfaces 34 engages and supports a corresponding arcuate section 18 of the outer stent 5. Since the radius of curvature of each of the lobed surfaces 34 is equal to that of the unspread stent (and therefore also to that of each of the arcuate sections 18), each of the lobed surfaces 34 contacts each of the arcuate sections 18 uniformly over its entire length and distributes the tension from the spring 8 in a uniform manner over the entire arcuate section 18, as shown in FIG. 4. Additionally, the lobed surfaces 34 aid in positioning the outer stent with respect to the slots of the spreading ring. Conversely, a portion 35 of the elevated lip 26 between the lobed surfaces contacts the outer stent base 6 at the location of the windows 17, and thus does not actually hold one of the arcuate sections 18. The lobed surfaces of the present invention have been found to be superior to a purely circular elevated lip by uniformly distributing the stress placed upon the outer stent 5 in its spread configuration. In contrast, a circular lip contacts the spread outer stent at only the ends of each of the arcuate sections 18, as shown in FIG. 13. This six-point contact concentrates the stress of spreading rather than uniformly distributing it.

Figure 5:
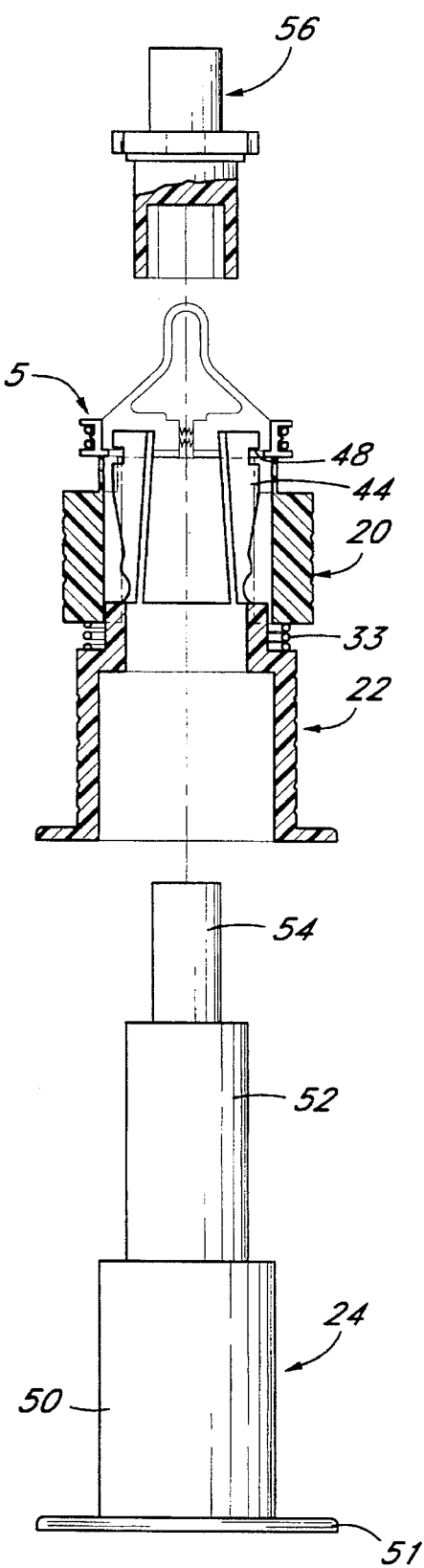
FIG. 5 is a cross-sectional view of a portion of the assembly tool holding the outer stent in a partially assembled state.

The expander 22 also has an overall annular configuration with an inner surface 40 and an outer surface 42, as shown in FIG. 1. An inner flange 41 is located within the expander on the inner wall surface 40. Finger grooves 43 formed in the outer wall of the expander 22 assist the surgeon in gripping the device during the spreading operation. A top portion 44 supports three flexible fingers 46 having outwardly facing grooves 48. The fingers 46 are angled radially inwardly at a small angle. During the spreading operation described below, the fingers 46 register within the slots 32 in the spreading ring. The grooves 48 of the fingers 46 engage with the inner flange 19 of the outer stent base, firmly securing it, as illustrated in FIG. 5.

Another feature of this invention is that the spreading tool 20 provides an optimum distribution of the spreading force by locating the fingers 46 so that they respectively contact the arcuate portions 18 of the outer stent at the middle of each of the scalloped portions 14. In order to achieve this result, the slots 32 in the spreading ring and the windows 36 in the elevated lip 26 are oriented to allow this contact point. In particular, the windows 36 bisect each of the lobed surfaces 34 of the elevated lip, since the fingers grip each arcuate surface 18 in its middle. The grooves 48 allow the fingers 46 to firmly hold the base 6 during the spreading operation. As described below, the flexible fingers 46 are moved outwardly during the spreading operation by the plunger 24 from a first position to a second, spread position. Since they contact the outer stent base 6, they move the arcuate sections 18 of the outer stent apart from each other against the tension force exerted by the spring 8.

Figure 6:
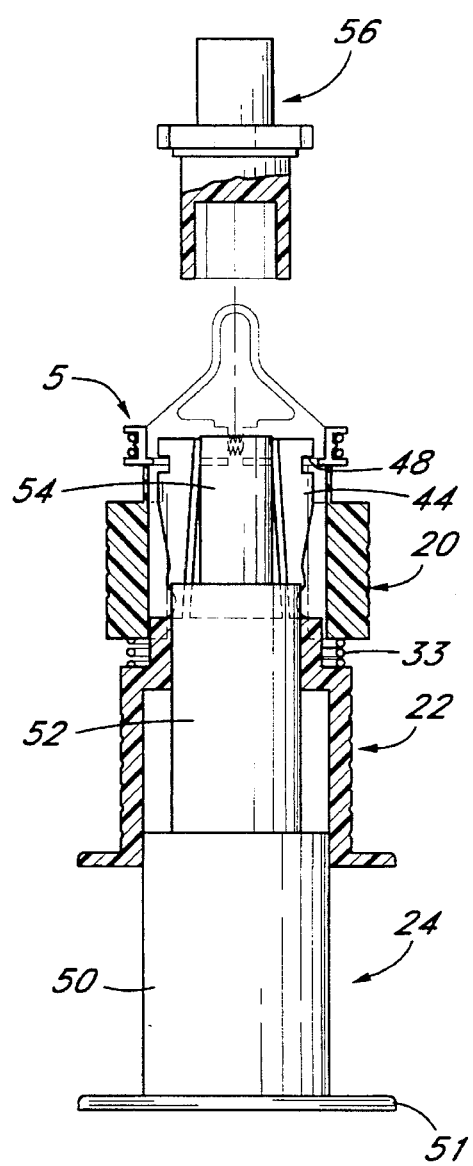
FIG. 6 is a cross sectional view of a portion of the assembly tool in a partially assembled state prior to spreading the outer stent base.

The plunger 24 has a series of integrally connected, generally cylindrical members having respective outer surfaces 50, 52 and 54. The plunger 24 is inserted into the inner surface 40 of the expander 22, as shown in FIG. 6. A grip 51 is provided at the proximal end of the plunger to aid the assembler during the insertion process. Outer surface 52 contacts the underside of each of the fingers 46, moving them outwardly by preloading them while another outer surface 50 fits snugly into the inner wall 40 of the expander to center the plunger and thus assure that each of the three fingers 46 is preloaded equally, as shown in FIGS. 7 and 8. When the plunger 24 is fully inserted into the expander 22, the top of the surface 50 contacts the expander inner flange 41, which prevents further movement and provides a positive indication that the plunger is fully inserted into the expander and the fingers 46 are correctly spread.

Another important feature of this invention is that rotation of the outer stent 5 with respect to the flexible fingers is positively prevented so as to ensure proper alignment of the outer stent during the expanding procedure. This important function is provided by the protective cap 56 shown in FIG. 1 which fits over the top outer surface 54 of the plunger. The protective cap 56 has slots 58 cut out of its lower surface 59 and recesses 60 cut out of a flanged portion 62. During initial assembly of the expander, spreading ring, and plunger, the protective cap 56 is fit over the outer surface 54 of the plunger, as shown in FIG. 7. The fingers 46 of the expander fit into the lower slots 58 of the shedding cap, and the posts 11 of the outer stent respectively register within the recesses 60 of the cap 56. This configuration of slots and recesses mated with fingers and posts therefore prevents rotational motion of the outer stent with respect to the fingers, thus preserving the proper alignment of stent to fingers.

The manner in which the spreader tool 10 of this invention is used during fabrication of the bioprosthetic valve is as follows: The spreading ring 20 is placed over the expander 22, the three flexible fingers 46 of the expander respectively sliding within the three slots 32 of the spreading ring 20, as shown in FIG. 11. Next, the outer stem 5 is mounted on the ends of the fingers 46 with each of the fingers 46 seated within the outer stent base 6. This is achieved by inserting each of the grooves 48 into the inner flange 19 of the outer stent base 6 at the middle of each arcuate section 18. The plunger 24 is then partially inserted into the expander 22 so that the surface 54 extends into the outer stent 6. The protective cap 56 is then placed over this top cylindrical surface 54 of the plunger, as shown in FIG. 7. The lower slots 58 of the cap are fitted over the fingers 46 of the expander, and the recesses 60 are brought into registry with the stent posts 11 to prevent rotation of the outer stent with respect to the fingers 46. These steps are advantageously performed before the tool kit is delivered to the surgeon to reduce the workload required in the operating room.

The surgeon or his assistant then uses the spreading tool 10 to spread the outer stent 5. This is performed by simply removing the protective cap 56 from the plunger 24 and fully inserting the plunger 24 into the expander 22, as shown in FIG. 8. This action causes the inwardly-angled fingers of the expander to be forced outwardly by engagement of their inner surface with the outer surface 52 of the plunger, causing spreading of the three arcuate portions 18 of the outer stent. The spring 33 then urges the elevated lip 26 of the spreading ring into position within the base of the outer stent 5, as shown in FIG. 9. The lobed surfaces 34 of the elevated lip support the arcuate sections 18 of the outer stent 5, and the outer stent is held in a spread position.

The surgeon or technician then removes the plunger 24 from the expander 22, whereupon the fingers 46 return to their normal position, thereby disengaging from the base of the outer stent 5. The expander 22 is then removed from the spreading ring 20, leaving the spreading ring holding the spread outer stent 5, as shown in FIG. 10.

Figure 12:
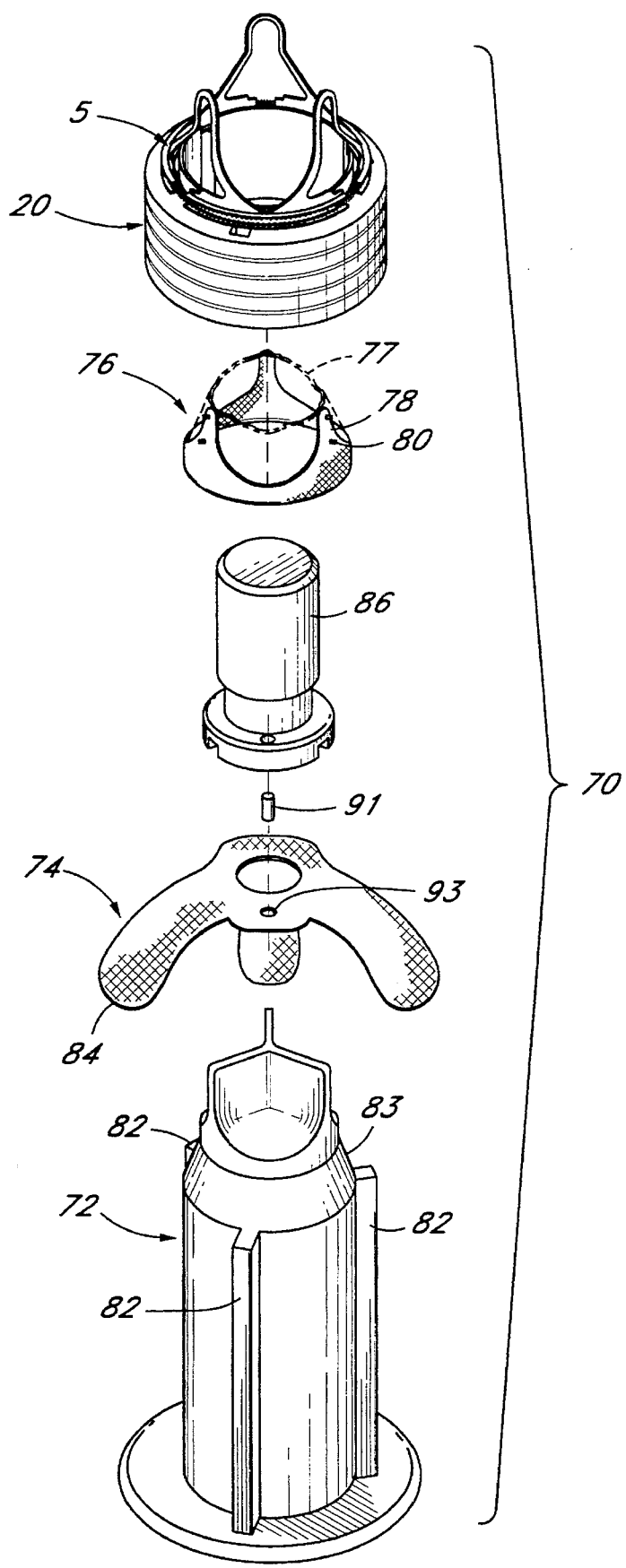
FIG. 12 is an exploded view of another portion of the assembly tool of the present invention.

The insertion tool 70 includes an assembly mandrel 72 and a shedding cap 74 for inserting an inner stent 76 wrapped with tissue 77 (shown in outline) into the spread outer stent 5, as shown in FIG. 12. The inner stent 76 includes posts 78 having outwardly-facing members 80 for holding the tissue. The tissue, either from the patient or a human or animal donor, is cut into the shape required to fabricate the heart valve leaflets and provided with holes to fit over the outward-facing members 80. The fabrication of the tissue is more fully set out in the present assignee's copending application Ser. No. 08/169,620, filed Dec. 17, 1993 and in U.S. Pat. No. 5,163,955, both of which are incorporated herein by reference.

The top surface of the mandrel 72 is advantageously configured, as shown in FIG. 12, to have three outwardly radiating leaves. To properly align the inner stent 76 with the mandrel, the assembler places the inner stent 76 over the assembly mandrel 24 so that each of the inner stent posts 78 is aligned with a corresponding leaf of this portion of the assembly mandrel.

Another important advantage of this invention is that the inner stent 76 is automatically precisely rotationally and axially aligned with the outer stent 5 during the insertion procedure. This is provided by indexing rails 82, which are disposed on the lower cylindrical surface of the assembly mandrel 72. These rails respectively mate with the axial slots 32 in the spreading ring during insertion of the mandrel into the spreading ring. Consequently, if the slots 32 are spaced 120 degrees apart from each other, the rails 82 will also be spaced 120 degrees apart. Each indexing rail is oriented to bisect one of the angles made by radii of the inner stent passing through the stent posts when the inner stent is aligned with each arm of the star-shaped top of the mandrel. These indexing rails thus allow the precise alignment of the posts of the inner and outer stents, as will be described below. The mandrel 72 also has a flanged portion 83 allowing the inner stent 76 to rest on the top portion of the assembly mandrel when placed thereon for insertion into the spread outer stent 5.

During manufacture of the bioprosthetic heat valve during open heart surgery, it is noted that not only is the valve precisely constructed in just a few minutes, but that the tissue used is carefully handled during the valve assembly and protected from abrasion. The present invention ensures that this is achieved by cap 74 (FIG. 12) composed of a very thin layer of shedding material, such as plastic. The shedding cap shown in FIG. 12 comprises three thin, planar leaves radiating from the center at 120-degree intervals, mounted to a cap or support 86 on top of the assembly mandrel 72 by means of a fastener 91 emplaced in an opening 93. The shedding cap 74 protects the tissue covering the inner stent posts from possible abrasion during the insertion of the inner stent into the spread outer stent. Consequently, in use, each leaf 84 of the shedding cap is placed over a corresponding inner stent post 78 of the inner stent mounted onto the mandrel 72.

In use, the surgeon or technician places the inner stent 76 over the top of the assembly mandrel 72, aligning each of the posts 78 of the stent with the corresponding projection of the top portion of the mandrel. Next, the surgeon drapes the shedding cap 74 over the tissue covering the posts of the inner stent 76. The surgeon then inserts the assembly mandrel 72 into the center of the spreading ring 20 containing the spread outer stent 5, making sure to align the indexing rails 82 with the axial slots 32 of the spreading ring. As noted above, this registry of the indexing rails 82 with the axial slots of the spreading ring 20 ensures that the posts of the inner and outer stents will be correctly aligned with each other. The surgeon pushes the assembly mandrel through the spreading ring, deploying the inner stent into the outer stent. When the inner and outer stents are fully mated, the indexing rails 82, passing through the spreading ring 20 into the windows 36 formed in the elevated lip of the spreading ring 20, will contact the outer stent base 6 and push the outer stent 5 off of the spreading ring 20. Following deployment of the inner stent into the outer stent, the outer stent base, no longer supported on the spreading ring lip, supplies a clamping force to the inner stent, ensuring that the stents remain mated. The indexing rails 82 therefore provide both rotational alignment of the outer and inner stents (by virtue of their angular orientation) and axial alignment of the stents, since they contact the outer stent base 6 and remove the outer stent from the spreading ring when the assembly operation is complete.

The surgeon then takes the completed valve assembly, tests it for leakage and competence as described in U.S. Pat. No. 5,163,955, places it on an insertion assembly, and implants it into the patient.

Thus, the heart valve assembly tool of the present invention provides a reliable, quick, and simple method of manufacturing bioprosthetic heart valves in an operating-room environment. The simplicity of the tool allows a technician to construct the valve in a few minutes while the surgeon is occupied with other tasks during the heart surgery. Additionally, the tool does not require the assembler to touch the outer stent of the valve while spreading it, minimizing the risk of damage. Finally, the provision of an indexing rail to the assembly mandrel ensures both precise axial and rotational alignment of the inner and outer stents with respect to each other.

Having described the invention in connection with certain specific embodiments thereof, it is to be understood that further modifications may now suggest themselves to those skilled in the art, and it is intended to include such modifications as fall within the scope of the appended claims.

What is claimed is:

1. An assembly tool for assembling a bioprosthetic heart valve having an inner stent with an annular base and a plurality of posts extending from the base along an axis of the valve, said inner stent covered with tissue, and an outer stent having an annular base and a plurality of posts extending from the base along an axis of the valve, said outer stent mating with and clamping said tissue to said inner stent, said assembly tool (i) expanding the base of said outer stent to a spread position so that the forces applied to said base uniformly distribute the stress on said base during the spreading operation and optimally apply the spreading forces to substantially the midpoint between adjacent posts, (ii) maintaining proper alignment of the outer stent with respect to said tool during the spreading procedure, (iii) precisely rotationally and axially aligning said inner stent and said outer stent during the mating of the outer stent to the inner stent, and (iv) protecting the tissue covering said inner stent during the assembly procedure, said assembly tool comprising:

an expander having three flexible fingers for engaging the inside of the base of the outer stent and applying an initial outward radial force to said base when said fingers are actuated to expand the outer stent from an unspread to a spread position, a spreading ring for maintaining the base in said spread position, said base having a plurality of lobed surfaces having an arcuate circumferential profile substantially corresponding in radius to the radius of the outer stent base in its unspread position so as to uniformly distribute the stress on said base during the spreading operation;

a plunger insertable into said expander, said plunger having a distal and a proximal end and distal, center, and proximal cylindrical members, said center member engaging the inner surfaces of each of said fingers and radially outwardly forcing said fingers when said plunger is inserted into said expander, said distal cylindrical member radially aligning said center cylindrical member with respect to said fingers of said expander when said plunger is inserted into said expander;

a protective cap engageable with said proximal surface of said plunger, said cap including three alignment slots engageable with the fingers of said expander, said cap further including an upper flange having three cutouts capable of registering with said posts of said outer stent spaced at equal intervals along said flange, said cutouts and said alignment slots cooperating to prevent rotational movement of said outer stent with respect to said fingers of said expander when said cutouts are registered with said outer stent and said alignment slots are engaged with said fingers;

an assembly mandrel for inserting said inner stent through said spreading ring into said outer stent when said outer stent is held on said spreading ring in a spread position, said assembly mandrel including a plurality of indexing rails engageable with said spreading ring, said indexing rails fixing the angular relationship of said spreading ring and said assembly mandrel when said mandrel is used to insert said inner stent into said outer stent; and a shedding cap placed over the tissue wrapped on said inner stent when said inner stent is placed on said assembly mandrel, said shedding cap protecting said tissue from abrasion during the insertion of said inner into said outer stent.

2. An assembly tool for assembling a bioprosthetic heart valve having an inner stent with an annular base and a plurality of posts extending from the base along an axis of the valve, said inner stent covered with tissue, and an outer stent having an annular base and a plurality of posts extending from the base along an axis of the valve, said outer stent mating with and clamping said tissue to said inner stent, said assembly tool comprising:

a spreading assembly engaging the base of said outer stent and forcing said outer stent into a spread position;

a mandrel for mating the inner stent to the outer stent when said outer stent is in a spread configuration; and indexing rails mounted to said mandrel, said indexing apparatus ensuring proper radial and axial alignment of said inner stent with said outer stent.

3. An assembly tool for assembling a bioprosthetic heart valve having an inner stent with an annular base and a plurality of posts extending from the base along an axis of the valve, said inner stent covered with tissue, and an outer stent having an annular base and a plurality of posts extending from the base along an axis of the valve, said outer stent mating with and clamping said tissue to said inner stent, said assembly tool expanding the base of said outer stent to a spread position so that the forces applied to said base uniformly distribute the stress on said base during the spreading operation, said assembly tool comprising:

an expander having three flexible fingers for engaging the inside of the base of the outer stent and applying an initial outward radial force to said base when said fingers are actuated to expand the outer stent from an unspread to a spread position;

a spreading ring for maintaining the base in said spread position;

a plunger insertable into said expander, said plunger engaging the inner surface of each of said fingers and radially outwardly forcing said fingers when said plunger is inserted into said expander; and an assembly mandrel for inserting said inner stent through said spreading ring into said outer stent when said outer stent is held on said spreading ring in a spread position, said assembly mandrel including a plurality of indexing rails engageable with said spreading ring, said indexing rails fixing the angular relationship of said spreading ring and said assembly mandrel when said mandrel is used to insert said inner stent into said outer stent.

4. The assembly tool of claim 3, further comprising a protective cap placed over said plunger and having a base and top portion, said base portion having a plurality of slots cut therein, said slots receiving the fingers of said expander, said top portion having a plurality of recesses, said recesses receiving the posts of said outer stent, said slots and recesses preventing rotation of said stent with respect to the fingers of said expander when said protective cap is placed over said plunger.

5. The assembly tool of claim 3, wherein said bottom portion of said mandrel further comprises a plurality of indexing rails, said indexing rails registering with the slots in said spreading ring to ensure that said posts of said inner and said outer stents are correctly aligned.

6. The assembly tool of claim 3, wherein said elevated lip further comprises a plurality of lobes, each of said lobes having a radius of curvature substantially equal to the inner radius of said outer stent, said lobes providing a surface for uniform contact between said elevated lip and the inner surfaces of said base of said outer stent.

7. The assembly tool of claim 3, wherein said shedding cap has a plurality of arms, each of said arms contacting one of the posts of said inner stent, said arms thereby protecting the tissue mounted on said inner stent from abrasion.

8. The tool of claim 3, further comprising a shedding cap placed over said tissue to protect said tissue from abrasion during the mating of said inner stent into said outer stent.

9. The assembly tool of claim 3, further comprising a spring disposed on said annular expander for urging the elevated lip of said spreading ring into contact with the annular base of said outer stent when said outer stent is in a spread position.

10. An assembly tool for assembling a bioprosthetic heart valve having an inner stent with an annular base and a plurality of posts extending from the base along an axis of the valve, said inner stent covered with tissue, and an outer stent having an annular base and a plurality of posts extending from the base along an axis of the valve, the base of said outer stent expandable from a rest position to a spread position, said outer stent mating with and clamping said tissue to said inner stent, said assembly tool comprising:

an annular spreading ring having inner and outer surfaces, a plurality of slots cut in said inner surface in an axial direction, and an elevated lip, said elevated lip including lobed surfaces configured to engage the annular base of said outer stent when said base is in a spread position;

an annular expander having inner and outer surfaces and a top surface with three fingers connected thereto, said outer surface capable of insertion into said spreading ring, each of said fingers registering with one of said slots cut in said inner surface of said spreading ring and each of said fingers engaging the annular base of said outer stent, said fingers movable from a rest position to a spread position, said fingers moving the base of said outer stent to a spread position when said fingers are moved to a spread position;

a plunger having cylindrical outer surfaces, said plunger engageable with said inner surface of said expander, said plunger outer surfaces forcing said fingers of said annular expander to said spread position when said plunger is inserted into said expander;

a mandrel having a base and a top portion, said top portion configured to secure said inner stent in place when said inner stent is placed over said top portion, said top portion engageable with said inner surface of said spreading ring to insert said inner stent into said outer stent when said outer stent is in a spread position; and a shedding cap covering said tissue on said inner stent and shielding said tissue mounted to the inner stent from abrasion when said inner stent is placed inside said outer stent.

11. A tool for assembling a bioprosthetic heart valve having an inner stent with an annular base and a plurality of posts extending from the base along an axis of the valve, said inner stent covered with tissue, and an outer stent having an annular base and a plurality of posts extending from the base along an axis of the valve, the base of said outer stent expandable from a rest position to a spread position, said outer stent mating with and clamping said tissue to said inner stent, said tool comprising:

an annular spreading ring having inner and outer surfaces, a plurality of slots cut in said inner surface in an axial direction, and an elevated lip having a plurality of lobes, each of said lobes having a radius of curvature substantially equal to the inner radius of said outer stent, said lobes providing a surface for uniform contact between said elevated lip and the inner surfaces of said base of said outer stent when said base is in a spread position;

an annular expander having inner and outer surfaces and a top surface with a plurality of fingers connected thereto, said outer surface capable of insertion into said spreading ring, each of said fingers registering with one of said slots cut in said inner surface of said spreading ring and each of said fingers engaging the annular base of said outer stent, said fingers movable from a rest position to a spread position, said fingers moving the base of said outer stent to a spread position when said fingers are moved to a spread position;

a plunger having cylindrical outer surfaces, said plunger engageable with said inner surface of said expander, said plunger outer surfaces forcing said fingers of said annular expander to said spread position when said plunger is inserted into said expander;

a mandrel having a base and a top portion, said top portion configured to secure said inner stent in place when said inner stent is placed over said top portion, said top portion engageable with said inner surface of said spreading ring to insert said inner stent into said outer stent when said outer stent is in a spread position, and said bottom portion having a plurality of indexing tangs, said indexing tangs registering with the slots in said spreading ring to ensure that said posts of said inner and said outer stents are correctly aligned; and a shedding cap covering said tissue on said inner stent and shielding said tissue mounted to the inner stent from abrasion when said inner stent is placed inside said outer stent.

* * * * *